（12) United States Patent
Kachlany et al.

(10) Patent No.: US 9,950,030 B2
(45) Date of Patent: Apr. 24, 2018

(54) TREATMENT AND DIAGNOSIS OF OCULAR DISEASE (71) Applicants: Actinobac Biomed, Inc., Kendall Park, NJ (US); Rutgers, The State University of New Jersey, New Brunswick, NJ (US)

(72) Inventors: Scott Kachlany, Bridgewater, NJ (US); Benjamin Belinka, Kendall Park, NJ (US)

(73) Assignees: RUTGERS, THE STATE UNIVERSITY OF NEW JERSEY, New Brunswick, NJ (US); ACTINOBAC BIOMED, INC., Kendall Park, NJ (US)

( * ) Notice: Subject to any disclaimer, the term of this patent is extended or adjusted under 35 U.S.C. 154(b) by 8 days.

(21) Appl. No.: 14/901,631

(22) PCT Filed: Jun. 27, 2014

(86) PCT No.: PCT/US2014/044567
§ 371 (c)(1),
(2) Date: Dec. 28, 2015

(87) PCT Pub. No.: WO2014/210454
PCT Pub. Date: Dec. 31, 2014

(65) Prior Publication Data
US 2016/0287662 A1 Oct. 6, 2016

Related U.S. Application Data (60) Provisional application No. 61/840,045, filed on Jun. 27, 2013.

(51) Int. Cl.
*A61K 38/16* (2006.01)
*A61K 9/00* (2006.01)

(52) U.S. Cl.
CPC .......... *A61K 38/164* (2013.01); *A61K 9/0048* (2013.01); *A61K 9/0051* (2013.01)

(58) Field of Classification Search
None
See application file for complete search history.

(56) References Cited

U.S. PATENT DOCUMENTS

2006/0252107 A1 11/2006 Kubota et al.
2012/0263644 A1 10/2012 Kachlany

FOREIGN PATENT DOCUMENTS

EP 2488198 A2 8/2012
WO 2012/125942 A1 9/2012

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Extended European Search Report dated Dec. 6, 2016 in European Patent Application No. 14817083.0 (8 pages).

* cited by examiner

*Primary Examiner* — Jennifer E Graser
(74) *Attorney, Agent, or Firm* — Fox Rothschild LLP (57) ABSTRACT This invention concerns compositions and methods of treating or diagnosing ocular disease.

11 Claims, 5 Drawing Sheets

SEQUENCE LISTING

```
<160> NUMBER OF SEQ ID NOS: 2

<210> SEQ ID NO 1
<211> LENGTH: 1055
<212> TYPE: PRT
<213> ORGANISM: Aggregatibacter actinomycetemcomitans

<400> SEQUENCE: 1

Met Ala Thr Thr Ser Leu Leu Asn Thr Lys Gln Gln Ala Ala Gln Phe
1               5                  10                  15

Ala Asn Ser Val Ala Asp Arg Ala Lys Glu Asn Ile Asp Ala Ala Lys
            20                  25                  30

Glu Gln Leu Gln Lys Ala Leu Asp Lys Leu Gly Lys Thr Gly Lys Lys
        35                  40                  45

Leu Thr Leu Tyr Ile Lys Asn Tyr Lys Lys Gly Asn Gly Leu Thr Ala
    50                  55                  60

Leu Ile Lys Ala Ala Gln Lys Leu Gly Ile Glu Val Tyr His Glu Gly
65                  70                  75                  80

Lys Asp Gly Pro Ala Leu Thr Asn Gly Ile Leu Asn Thr Gly Lys Lys
                85                  90                  95

Leu Leu Gly Leu Thr Glu Arg Gly Leu Thr Leu Phe Ala Pro Glu Leu
            100                 105                 110

Asp Lys Trp Ile Gln Gly Asn Lys His Leu Ser Asn Ser Val Gly Ser
        115                 120                 125

Thr Gly Asn Leu Thr Lys Ala Ile Asp Lys Val Gln Ser Val Leu Gly
    130                 135                 140

Thr Leu Gln Ala Phe Leu Asn Thr Ala Phe Ser Gly Met Asp Leu Asp
```

-continued

```
            145                 150                 155                 160
        Ala Leu Ile Lys Ala Arg Gln Asn Gly Lys Asn Val Thr Asp Val Gln
                        165                 170                 175
        Leu Ala Lys Ala Ser Leu Asn Leu Ile Asn Glu Leu Ile Gly Thr Ile
                        180                 185                 190
        Ser Ser Ile Thr Asn Asn Val Asp Thr Phe Ser Lys Gln Leu Asn Lys
                        195                 200                 205
        Leu Gly Glu Ala Leu Gly Gln Val Lys His Phe Gly Ser Phe Gly Asp
                        210                 215                 220
        Lys Leu Lys Asn Leu Pro Lys Leu Gly Asn Leu Gly Lys Gly Leu Gly
        225                 230                 235                 240
        Ala Leu Ser Gly Val Leu Ser Ala Ile Ser Ala Ala Leu Leu Leu Ala
                        245                 250                 255
        Asn Lys Asp Ala Asp Thr Ala Thr Lys Ala Ala Ala Ala Ala Glu Leu
                        260                 265                 270
        Thr Asn Lys Val Leu Gly Asn Ile Gly Lys Ala Ile Thr Gln Tyr Leu
                        275                 280                 285
        Ile Ala Gln Arg Ala Ala Ala Gly Leu Ser Thr Thr Gly Pro Val Ala
                        290                 295                 300
        Gly Leu Ile Ala Ser Val Val Ser Leu Ala Ile Ser Pro Leu Ser Phe
        305                 310                 315                 320
        Leu Gly Ile Ala Lys Gln Phe Asp Arg Ala Arg Met Leu Glu Glu Tyr
                        325                 330                 335
        Ser Lys Arg Phe Lys Lys Phe Gly Tyr Asn Gly Asp Ser Leu Leu Gly
                        340                 345                 350
        Gln Phe Tyr Lys Asn Thr Gly Ile Ala Asp Ala Ala Ile Thr Thr Ile
                        355                 360                 365
        Asn Thr Val Leu Ser Ala Ile Ala Ala Gly Val Gly Ala Ala Ser Ala
                        370                 375                 380
        Gly Ser Leu Val Gly Ala Pro Ile Gly Leu Leu Val Ser Ala Ile Thr
        385                 390                 395                 400
        Ser Leu Ile Ser Gly Ile Leu Asp Ala Ser Lys Gln Ala Val Phe Glu
                        405                 410                 415
        His Ile Ala Asn Gln Leu Ala Asp Lys Ile Lys Ala Trp Glu Asn Lys
                        420                 425                 430
        Tyr Gly Lys Asn Tyr Phe Glu Asn Gly Tyr Asp Ala Arg His Ser Ala
                        435                 440                 445
        Phe Leu Glu Asp Ser Leu Lys Leu Phe Asn Glu Leu Arg Glu Lys Tyr
                        450                 455                 460
        Lys Thr Glu Asn Ile Leu Ser Ile Thr Gln Gln Gly Trp Asp Gln Arg
        465                 470                 475                 480
        Ile Gly Glu Leu Ala Gly Ile Thr Arg Asn Gly Asp Arg Ile Gln Ser
                        485                 490                 495
        Gly Lys Ala Tyr Val Asp Tyr Leu Lys Lys Gly Glu Glu Leu Ala Lys
                        500                 505                 510
        His Ser Asp Lys Phe Thr Lys Gln Ile Leu Asp Pro Ile Lys Gly Asn
                        515                 520                 525
        Ile Asp Leu Ser Gly Ile Lys Gly Ser Thr Thr Leu Thr Phe Leu Asn
                        530                 535                 540
        Pro Leu Leu Thr Ala Gly Lys Glu Glu Arg Lys Thr Arg Gln Ser Gly
        545                 550                 555                 560
        Lys Tyr Glu Phe Ile Thr Glu Leu Lys Val Lys Gly Arg Thr Asp Trp
                        565                 570                 575
```

```
Lys Val Lys Gly Val Pro Asn Ser Asn Gly Val Tyr Asp Phe Ser Asn
            580             585             590

Leu Ile Gln His Ala Val Thr Arg Asp Asn Lys Val Leu Glu Ala Arg
        595             600             605

Leu Ile Ala Asn Leu Gly Ala Lys Asp Tyr Val Phe Val Gly Ser
610             615             620

Gly Ser Thr Ile Val Asn Ala Gly Asp Gly Tyr Asp Val Val Asp Tyr
625             630             635             640

Ser Lys Gly Arg Thr Gly Ala Leu Thr Ile Asp Gly Arg Asn Ala Thr
            645             650             655

Lys Ala Gly Gln Tyr Lys Val Glu Arg Asp Leu Ser Gly Thr Gln Val
            660             665             670

Leu Gln Glu Thr Val Ser Lys Gln Glu Thr Lys Arg Gly Lys Val Thr
        675             680             685

Asp Leu Leu Glu Tyr Arg Asn Tyr Lys Leu Asp Tyr Tyr Tyr Thr Asn
        690             695             700

Lys Gly Phe Lys Ala His Asp Glu Leu Asn Ser Val Glu Glu Ile Ile
705             710             715             720

Gly Ser Thr Leu Arg Asp Lys Phe Tyr Gly Ser Lys Phe Asn Asp Val
            725             730             735

Phe His Gly His Asp Gly Asp Leu Ile Tyr Gly Tyr Asp Gly Asp
            740             745             750

Asp Arg Leu Tyr Gly Asp Asn Gly Asn Asp Glu Ile His Gly Gly Gln
            755             760             765

Gly Asn Asp Lys Leu Tyr Gly Gly Ala Gly Asn Asp Arg Leu Phe Gly
        770             775             780

Glu Tyr Gly Asn Tyr Leu Asp Gly Gly Glu Gly Asp His Leu
785             790             795             800

Glu Gly Gly Asn Gly Ser Asp Ile Leu Arg Gly Gly Ser Gly Asn Asp
            805             810             815

Lys Leu Phe Gly Asn Gln Gly Asp Asp Leu Leu Asp Gly Gly Glu Gly
            820             825             830

Asp Asp Gln Leu Ala Gly Gly Glu Gly Asn Asp Ile Tyr Val Tyr Arg
            835             840             845

Lys Glu Tyr Gly His His Thr Ile Thr Glu His Ser Gly Asp Lys Asp
            850             855             860

Lys Leu Ser Leu Ala Asn Ile Asn Leu Lys Asp Val Ser Phe Glu Arg
865             870             875             880

Asn Gly Asn Asp Leu Leu Lys Thr Asn Asn Arg Thr Ala Val Thr
            885             890             895

Phe Lys Gly Trp Phe Ser Lys Pro Asn Ser Ser Ala Gly Leu Asp Glu
        900             905             910

Tyr Gln Arg Lys Leu Leu Glu Tyr Ala Pro Glu Lys Asp Arg Ala Arg
        915             920             925

Leu Lys Arg Gln Phe Glu Leu Gln Arg Gly Lys Val Asp Lys Ser Leu
        930             935             940

Asn Asn Lys Val Glu Glu Ile Ile Gly Lys Asp Gly Glu Arg Ile Thr
945             950             955             960

Ser Gln Asp Ile Asp Asn Leu Phe Asp Lys Ser Gly Asn Lys Lys Thr
            965             970             975

Ile Ser Pro Gln Glu Leu Ala Gly Leu Ile Lys Asn Lys Gly Lys Ser
            980             985             990
```

```
        Ser Ser Leu Met Ser Ser Ser Arg Ser Ser Ser Met Leu Thr Gln Lys
            995                 1000                1005

Ser Gly Leu Ser Asn Asp Ile Ser Arg Ile Ile Ser Ala Thr Ser
            1010                1015                1020

Gly Phe Gly Ser Ser Gly Lys Ala Leu Ser Ala Ser Pro Leu Gln
            1025                1030                1035

Thr Asn Asn Asn Phe Asn Ser Tyr Ala Asn Ser Leu Ala Thr Thr
            1040                1045                1050

Ala Ala
            1055

<210> SEQ ID NO 2
<211> LENGTH: 3168
<212> TYPE: DNA
<213> ORGANISM: Aggregatibacter actinomycetemcomitans

<400> SEQUENCE: 2
atggcaacta cttcactgct aaatacaaaa cagcaagctg cacagtttgc aaattcagtt     60
gcagatagag ctaaggaaaa tattgatgct gcaaagaaac aattgcaaaa ggcgttagat    120
aaattaggga agacaggtaa gaaattaact ttatatatcc ctaagaatta caaaaaagga    180
aatggtctta ctgcgcttat aaaagcagca cagaagttag ggattgaagt atatcatgaa    240
gggaaagacg gcccggcatt aactaatggt attttaaata ctgggaaaaa attacttggt    300
cttaccgaac gaggtttaac tttatttgct ccggaattag ataaatggat tcaaggtaat    360
aaacatttaa gtaattctgt gggtagtact ggaaatttga caaaagcgat agataaggtt    420
cagagtgttc ttggtacgtt acaagcgttt ttgaacaccg cattttcggg catggattta    480
gatgccttaa ttaaagcccg tcaaatggt aaaaatgtaa cagatgtaca gctagcaaaa    540
gccagtctta acctgattaa tgaattgatt ggtactattt ctagcattac aaataatgta    600 gatactttt ctaaacaact taataagtta ggtgaagcac taggacaagt aaaacatttt    660
ggtagttttg gagataaatt aaagaattta cctaagttag gtaatcttgg aaaaggttta    720
ggtgcattat ccggtgtatt gtcggctata tcagcggctc tattacttgc aaataaagat    780
gctgatactg caacgaaagc agcggctgca gctgaattga caaataaagt gctaggtaac    840
atcggtaaag cgatcacaca atacttgatt gctcaacgtg ctgcagcggg gcttctact    900 acgggacctg tcgcagggtt aattgcctct gtggtcagct ggcaatcag ccctttgtct    960 ttcctaggta ttgcgaaaca atttgatcgt gcgagaatgc ttgaggaata ctcgaaacgc   1020
tttaagaaat ttggttataa cggcgatagt ttacttggtc aattctacaa aaatacaggg   1080
atcgcagatg ctgcgattac aacgattaac actgtattaa gtgctattgc agcaggggtt   1140
ggtgcagcct ccgccggttc tttagttggt gcgccaatcg gtttgttagt gagtgcgatt   1200
accagcttaa tttcaggaat tcttgatgct tctaaacaag ccgttttga acatatcgcg   1260 aatcagctcg ccgataaaat taagcatgg gagaataagt acgtaagaa ttactttgaa   1320 aatggctatg atgcccgtca ttccgccttc ttggaagatt cactaaaatt atttaatgag   1380
ttacgtgaaa aatataaaac cgaaaatata ttatctatca ctcaacaagg ttgggatcag   1440
cgcattggtg aattagcagg tatcactcgt aatgagatc gtattcaaag tggtaaagct   1500
tatgtggatt atttgaaaaa gggtgaggag cttgcaaagc atagcgataa attcactaaa   1560
cagattttag atccaatcaa aggtaatatt gatcttcgg gtataaaagg ttctaccact   1620
ctaacttttt taaatccgtt gttaaccgca ggtaaggaag aacggaaaac acgtcagtca   1680
```

```
ggtaaatatg aatttattac tgaattaaaa gtaaaaggac gtaccgattg gaaggtaaaa      1740
ggtgttccta attctaatgg tgtatatgat ttttctaact taattcaaca tgccgttaca      1800
cgtgataata aagttctaga agcaagatta attgctaatt tgggtgctaa agatgattat     1860
gtttttgtcg gatccggttc aacaatagtt aatgctggag acggttatga tgtggtggac     1920
tatagtaaag gtcgcaccgg tgcattaaca atcgacggtc gtaatgctac taaagccgga     1980
caatataagg ttgaaagaga tcttagcggt actcaagtct tgcaggaaac cgtatcaaag     2040
caagaaacta aacgagggaa ggttaccgat ctacttgaat atcgtaacta taaattagat     2100
tactattata cgaataaggg ctttaaagct catgatgaat taaactcagt agaggaaatt     2160
atcggcagca cactacgtga taaattttat ggttctaaat ttaatgatgt tttccatggt     2220
cacgatggcg atgatttgat ttatggttat gatggcgatg atcgtttgta tggcgataat     2280
gggaatgacg aaattcatgg cggccaaggt aatgataagc tctatggtgg tgccggtaac     2340
gataggctct ttggtgaata tggcaacaac tatcttgacg gtggagaagg cgacgaccac     2400
ttagagggag gcaatggttc cgatattcta agaggtggaa gtggcaatga taagttgttt     2460
ggaaaccaag gagatgattt acttgacggt ggagaaggcg atgaccaact tgccggtgga     2520
gaaggaaatg atatttatgt ttaccgtaaa gaatatgggc accacactat tacggaacat     2580
agcggtgata aagataaatt atcattagca aatatcaatc tcaaagatgt gtcatttgag     2640
cgtaacggca atgatctact attgaaaaca ataaatagaa cagcagtaac atttaaagga     2700
tggtttagta aacctaattc atcggcagga ttagatgagt atcaaagaaa acttcttgaa     2760
tacgcacctg aaaaggatcg tgcacgactt aagagacaat ttgagttaca gcgaggtaaa     2820
gtcgacaaat cactcaataa taaagttgaa gaaattatcg gtaaagatgg ggagcggatt     2880
acttcgcaag acattgataa tctttttgat aagagtggga acaaaaagac aatttcacct     2940
caagagcttg ccggacttat taagaataaa ggtaagtcaa gtagccttat gtcttcttct    3000
cgttcgtcaa gtatgcttac acaaaagtcc ggtttgtcaa atgatattag tcgtattatt    3060
tcagcaacca gtggtttttgg ttcatccggt aaagcgttat ccgcttcgcc attgcagacc    3120
aataataact ttaactctta cgcaaattcg ttagcaacta ctgcggcc                 3168
```

TREATMENT AND DIAGNOSIS OF OCULAR DISEASE

CROSS-REFERENCE TO RELATED APPLICATION

This application is the 371 national phase of PCT/US14/44567, filed Jun. 27, 2014, which claims priority of U.S. Provisional Application No. 61/840,045 filed on Jun. 27, 2013. The contents of both applications are incorporated herein by reference in their entireties.

FIELD OF THE INVENTION

This invention relates to pharmaceutical compositions, reagents and methods for treating or diagnosing ocular disease.

BACKGROUND OF THE INVENTION

Ocular inflammatory disease is a general term embracing a number of diseases and conditions in which inflammation affects the eye or surrounding tissues. Inflammation is due to abnormal activation and migration of white blood cells to regions for example, the conjunctival epithelium and tear glands. Although some treatments are presently available, many possess significant side effects or are not very effective in alleviating all symptoms. Thus, there is a need for drugs and reagents for treatment and diagnosis of ocular inflammatory disease.

SUMMARY OF THE INVENTION

This invention relates to treatment and diagnosis of ocular inflammatory disease using leukotoxin (LtxA), a bacterial protein.

At least one aspect of the invention is directed to a method of treating a disease characterized by ocular inflammation, the method comprising administering a pharmaceutical composition to a subject in need of such treatment in an amount effective to reduce said inflammation, wherein the pharmaceutical composition comprises a leukotoxin and a pharmaceutically acceptable carrier, and wherein the disease is an ocular inflammatory disease. The ocular inflammatory disease maybe keratoconjunctivitis sicca, diabetic retinopathy, diabetic macula edema, Sjogren syndrome, dry eye, scleritis, birdshot retinochoriodopathy, ocular cicatricial pemphigoidm, keratitis, sympathetic ophthalmia, vogt-koy-anagi harada, fuchs' heterochromic iridocyclitis, uveitis, pars planitis, episcleritis, optic neuritis, orbital pseudotumor, retinal vasculitis, ocular allergy, and chronic conjunctivitis.

Another aspect of the invention is directed to a method of reducing ocular inflammation in an ocular region within a subject in need thereof, characterized by increased levels of activated white blood cells in a subject in need thereof, the method comprising administering to the subject an amount of a pharmaceutical composition in amount effective to reduce said ocular inflammation, wherein the pharmaceutical composition comprises a leukotoxin and a pharmaceutically acceptable carrier. The ocular inflammation may be caused by an infection, autoimmune disease, allergen, ocular trauma, and ocular allograft rejection. The infection may be a viral, bacterial, or a fungal infection.

In at least one embodiment, the leukotoxin is LtxA, prepared from *Aggregatibacter actinomycetemcomitans*. In yet another embodiment, LtxA has at least 90% homology with the peptide according to SEQ ID NO: 1.

In another embodiment, the pharmaceutical composition comprising leukotoxin is administered topically to the ocular region. In another embodiment, the pharmaceutical composition is in a form suitable for topical administration. In another embodiment, the pharmaceutical composition is formulated for and administered by using an eye drop dispenser. In another embodiment, the pharmaceutically acceptable carrier is an eye gel, eye cream, suspension-type eye drops, eye wash, ointment, gel, liposomal dispersion, colloidal microparticle suspension, implant or a contact lens.

In another embodiment the amount of the pharmaceutical composition comprising leukotoxin administered to a subject in need thereof is effective to reduce local cytokine levels in the ocular region. One or more of the following cytokines expression levels are reduced, IL-4, IL-5, IL-9, IL17F and IL-23α.

Another aspect of the invention is directed to a kit comprising a pharmaceutically effective amount of leukotoxin for the treatment of an ocular inflammatory disease. The kit may contain multiple doses of a pharmaceutical composition comprising an effective amount of leukotoxin to treat an ocular inflammatory disease or to reduce ocular inflammation characterized by the increase of activated white blood cells in the ocular region that express a greater level of LFA-1 compared to white blood cells from a normal healthy subject.

DETAILED DESCRIPTION OF THE INVENTION

This invention relates to reagents and methods for treating or diagnosing ocular inflammatory disease and incorporates the discovery that administering LxA to a subject suffering ocular inflammation characterized by activated inflammatory cells expressing LFA-1 results in the depletion of the activated inflammatory cells.

LFA-1, a β2-integrin on the surface of white blood cells, is composed of CD11a and CD18 and involved in immune cell migration and signaling. In the absence of infection, circulating WBCs express a "resting state" LFA-1 on their surface. Inflammatory cytokines cause LFA-1 to assume an active conformation, which results in binding of activated LFA-1 to intercellular adhesion molecule-1 (ICAM-1) on the surface of endothelial cells. The interaction between LFA-1 and ICAM-1 results in migration of WBCs across the endothelial barrier and into the infected tissue. It has now been discovered that LtxA targets inflammatory white blood cells WBCs that express the activated conformation of LFA-1 on their surface that migrate to the eye and surrounding tissue resulting in ocular inflammation and local organ damage.

Ocular inflammatory disease is a general term for inflammation affecting the ocular region. The ocular region means any part of the eye or surrounding tissue, as known by one with ordinary skill in the art. Inflammation involving the eye can range from the familiar allergic conjunctivitis of hay fever to rare, potentially blinding conditions such as uveitis, scleritis, episcleritis, optic neuritis, keratitis, orbital pseudotumor, retinal vasculitis, and chronic conjunctivitis.

Broadly speaking, if inflammation develops in the eye(s), or in the optic nerve, blood vessels, muscles or other tissues that surround the eye, the resulting illness is referred to as an ocular inflammatory disease.

The location of the inflammation may govern the diagnostic name for the ocular inflammatory disease. For example, uveitis is inflammation in the uveal tract; scleritis is inflammation of the sclera, pars planitis is inflammation of the pars plana, and so forth. The treatment of ocular inflammatory disease is aimed at reducing inflammation. Ocular inflammation can occur for many reasons for example, as a result of an infection, an autoimmune disorder, trauma to the eye, or allergies.

LtxA

LtxA is a ~115 kDa protein produced by the Gram negative bacterium *Aggregatibacter actinomycetemcomitans* (Kachlany, S. C. 2010. J Dent Res 89:561-570.). LtxA specifically kills leukocytes of humans and Old World Primates by forming pores in the membrane and causing apoptosis or necrosis (Mangan et al., 1991. Infect Immun 59:3267-72.). LtxA binds specifically to LFA-1 and cells that lack LFA-1 are resistant to its toxicity (Kachlany, S. C. et al., 2010. Leukemia Research 34:777-85.). For example, LtxA is not active against human red blood cells, human epithelial cells, rat cells, or mouse cells. LtxA also remains active in the presence of human peripheral blood.

Many LtxA preparations can be used, highly purified LtxA is preferred. Examples include LtxA polypeptide purified from *Aggregatibacter actinomycetemcomitans* (SEQ ID NO: 1 shown above) and other variants having substantially the same biological activity as that having the sequence of SEQ ID NO: 1. It was discovered that *Aggregatibacter actinomycetemcomitans* secreted active LtxA into culture supernatants (Kachlany, S. C., et al. 2000. Infect Immun 68:6094-100) and an efficient method for its purification was described in Kachlany, S. C., et al. 2002. Protein Expr Purif 25:465-71. This method can therefore be used to prepare isolated or purified LtxA polypeptide. In one example, a purification procedure of the toxin involves:
 a. inoculating a single colony of *Aggregatibacter actinomycetemcomitans* into a fresh broth and growing cultures;
 b. adding the growing cultures to fresh broth, adding glass beads and incubating;
 c. centrifuging the incubated culture, forming a pellet and a supernatant;
 d. filtering the supernatant through a membrane to provide a filtered supernatant;
 e. mixing (NH4)2SO4 and the filtered supernatant together to form a mixture;
 f. centrifuging the mixture to form a mixture pellet;
 g. resuspending the mixture pellet in buffer to form a protein resuspension;
 h. passing the protein resuspension through a column; and
 i. collecting the protein eluting off the column.

See also PCT/US2006/45258 (WO 2007/062150); US Application 20090075883 (U.S. Ser. No. 12/154,843) and PCT/US10/52453 (WO 2011/047011). The contents of these documents are incorporated herein by reference.

An "isolated polypeptide" refers to a polypeptide that has been separated from other proteins, lipids, and nucleic acids with which it is naturally associated. The term "polypeptide" and "protein" can be used interchangeably when referring to LtxA. The polypeptide constitutes at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide of the invention can be purified from a natural source, produced by recombinant DNA techniques, or by chemical methods. A functional equivalent of LtxA refers to a polypeptide derivative of the LtxA polypeptide, e.g., a protein having one or more point mutations, insertions, deletions, truncations, a fusion protein, or a combination thereof. It retains substantially the activity of the LtxA polypeptide, i.e., the ability to target and kill WBCs that express the activated conformation of LFA-1 on their surface while having little or no toxic effect on other cells or organs in the body. The isolated polypeptide can contain SEQ ID NO: 1 or a functional fragment of SEQ ID NO: 1. In general, the functional equivalent is at least 75% (e.g., any number between 75% and 100%, inclusive, e.g., 70%, 80%, 85%, 90%, 95%, and 99%) identical to SEQ ID NO: 1.

All of naturally occurring LtxA, genetic engineered LtxA, and chemically synthesized LtxA can be used to practice the invention disclosed herein. LtxA obtained by recombinant DNA technology may have the same amino acid sequence as naturally a occurring LtxA (SEQ ID NO: 1) or an functionally equivalent thereof. The term "LtxA" also covers chemically modified LtxA. Examples of chemically modified LtxA include LtxA subjected to conformational change, addition or deletion of a sugar chain, and LtxA to which a compound such as polyethylene glycol has been bound. Once purified and tested by standard methods or according to the method described in the examples below, LtxA can be included in a pharmaceutical composition, e.g., a topical composition.

The amino acid composition of the LtxA polypeptide described herein may vary without disrupting the ability of the polypeptide to target and kill WBCs. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in SEQ ID NO: 1 is preferably replaced with another amino acid residue from the same side chain family. Alternatively, mutations can be introduced randomly along all or part of SEQ ID NO: 1, such as by saturation mutagenesis, and the resultant mutants can be screened for the ability to improve the ocular condition and/or to identify mutants that retain the activity as described below in the examples.

A LtxA polypeptide as described in this invention can be obtained as a naturally occurring polypeptide or a recombinant polypeptide. To prepare a recombinant polypeptide, a nucleic acid encoding it (e.g., SEQ ID NO: 2) can be linked to another nucleic acid encoding a fusion partner, e.g., glutathione-s-transferase (GST), 6×-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

Pharmaceutical Compositions

The present invention also provides a pharmaceutical composition that contains LtxA and a pharmaceutically acceptable carrier suitable for ocular administration. Examples of pharmaceutically acceptable carriers include, but are not limited to eye gel, eye cream, suspension-type eye drops, eye wash, ointment, gel, liposomal dispersion, colloidal microparticle suspension, contact lens, and the like, and other preparations known in the art to be suitable for ocular administration. As such, the pharmaceutical compositions of the present invention containing LtxA may be administered using commonly known devices configured for the delivery of the pharmaceutical compositions in the form of to the region surrounding the eye. An ocular insert, may also comprise a biodegradable controlled release polymeric matrix. The ocular insert can be implanted in the conjunctiva, sclera, pars plana, anterior segment, or posterior segment of the eye. Implants provide for controlled release of the pharmaceutical composition to the ocular surface, typically sustain release of LtxA over an extended time period. The pharmaceutically acceptable carrier of the pharmaceutical composition of the invention may comprise a wide variety of non-active ingredients which are useful for formulation purposes and which do not materially affect the novel and useful properties of LtxA.

By a "pharmaceutically acceptable" or "ophthalmologically acceptable" component, means a component that is not biologically or otherwise undesirable, i.e., the component may be incorporated into a pharmaceutical composition of the invention and administered topically to a patient's eye without causing any undesirable biological effects or interacting in a deleterious manner with any of the other components of the formulation composition in which it is contained. When the term "pharmaceutically acceptable" is used to refer to a component other than a pharmacologically active agent, it is implied that the component has met the required standards of toxicological and manufacturing testing or that it is included on the Inactive Ingredient Guide prepared by the U.S. Food and Drug Administration.

Suitable thickeners will be known to those of ordinary skill in the art of ophthalmic formulation, and include, by way of example, cellulosic polymers such as methylcellulose (MC), hydroxyethylcellulose (HEC), hydroxypropylcellulose (HPC), hydroxypropylmethylcellulose (HPMC), and sodium carboxymethylcellulose (NaCMC), and other swellable hydrophilic polymers such as polyvinyl alcohol (PVA), hyaluronic acid or a salt thereof (e.g., sodium hyaluronate), and crosslinked acrylic acid polymers commonly referred to as "carbomers". The preferred amount of any thickener is such that a viscosity in the range of about 15 cps to 25 cps is provided, as a solution having a viscosity in the aforementioned range is generally considered optimal for both comfort and retention of the formulation in the eye. Any suitable isotonic agents and buffering agents commonly used in ophthalmic formulations may be used, providing that the osmotic pressure of the solution does not deviate from that of lachrimal fluid by more than 2-3% and that the pH of the formulation is maintained in the range of about 6.5 to about 8.0, preferably in the range of about 6.8 to about 7.8, and optimally at a pH of about 7.4. Preferred buffering agents include carbonates such as sodium and potassium bicarbonate.

The pharmaceutical compositions of the invention may also be prepared as a hydrogel, dispersion, or colloidal suspension. Hydrogels are formed by incorporation of a swellable, gel-forming polymer such as those set forth above as suitable thickening agents (i.e., MC, HEC, HPC, HPMC, NaCMC, PVA, or hyaluronic acid or a salt thereof, e.g., sodium hyaluronate), except that a formulation referred to in the art as a "hydrogel" typically has a higher viscosity than a formulation referred to as a "thickened" solution or suspension. In contrast to such preformed hydrogels, a pharmaceutical composition may also be prepared so as to form a hydrogel in situ following application to the eye. Such gels are liquid at room temperature but gel at higher temperatures (and thus are termed "thermoreversible" hydrogels), such as when placed in contact with body fluids. Biocompatible polymers that impart this property include acrylic acid polymers and copolymers, N-isopropylacrylamide derivatives, and ABA block copolymers of ethylene oxide and propylene oxide. The pharmaceutical compositions can also be prepared in the form of a dispersion or colloidal suspension. Preferred dispersions are liposomal, in which case the pharmaceutical composition is enclosed within "liposomes," microscopic vesicles composed of alternating aqueous compartments and lipid bilayers. Colloidal suspensions are generally formed from microparticles, i.e., from microspheres, nanospheres, microcapsules, or nanocapsules, wherein microspheres and nanospheres are generally monolithic particles of a polymer matrix in which the pharmaceutical composition is trapped, adsorbed, or otherwise contained, while with microcapsules and nanocapsules, the formulation is actually encapsulated.

The pharmaceutically acceptable ophthalmic carrier used with the pharmaceutical composition of the invention may be of a wide range of types known to those of skill in the art. For example, the pharmaceutical compositions of the invention can be provided as an ophthalmic solution or suspension, in which case the carrier is at least partially aqueous. The pharmaceutical compositions may also be ointments, in which case the pharmaceutically acceptable carrier comprises an ointment base. Preferred ointment bases herein have a melting or softening point close to body temperature, and any ointment bases commonly used in ophthalmic preparations may be advantageously employed. Common ointment bases include petrolatum and mixtures of petrolatum and mineral oil.

The pharmaceutical composition may also be incorporated into a sterile ocular insert that provides for controlled release of the formulation over an extended time period, generally in the range of about 12 hours to 60 days, and possibly up to 12 months or more, following implantation of the insert into the conjunctiva, sclera, or pars plana, or into the anterior segment or posterior segment of the eye. One type of ocular insert is an implant in the form of a monolithic polymer matrix that gradually releases the pharmaceutical composition to the eye through diffusion and/or matrix degradation. With such an insert, it is preferred that the polymer be completely soluble and or biodegradable (i.e., physically or enzymatically eroded in the eye) so that removal of the insert is unnecessary. These types of inserts are well known in the art, and are typically composed of a water-swellable, gel-forming polymer such as poly ethylene glycol, collagen, polyvinyl alcohol, or a cellulosic polymer. Another type of insert that can be used to deliver the present formulation is a diffusional implant in which the formulation is contained in a central reservoir enclosed within a permeable polymer membrane that allows for gradual diffusion of the pharmaceutical composition out of the implant. Osmotic inserts may also be used, i.e., implants in which the pharmaceutical composition is released as a result of an increase in osmotic pressure within the implant following application to the eye and subsequent absorption of tears.

The term "controlled release" refers to an agent-containing formulation or fraction thereof in which release of the agent is not immediate, i.e., with a "controlled release" formulation, administration does not result in immediate release of the agent into an absorption pool. The term is used interchangeably with "nonimmediate release" as defined in Remington: The Science and Practice of Pharmacy, Nineteenth Ed. (Easton, Pa.: Mack Publishing Company, 1995). In general, the term "controlled release" as used herein refers to "sustained release" rather than to "delayed release" formulations. The term "sustained release" (synonymous with "extended release") is used in its conventional sense to refer to a formulation that provides for gradual release of an agent over an extended period of time.

In an embodiment, the LtxA is released over a period of at least 12 hours, at least 18 hours, at least 24 hours, at least 48 hours, at least 3 days, at least 7 days, at least 14 days, at least 30 days, at least 60 days, at least 90 days, at least 100 days, at least 120 days, at least 150 days, at least 180 days, or even longer.

The LtxA or pharmaceutical composition can be administered, as described herein, according to any of a number of standard methods including, but not limited to injection, nasal spray, time-release implant, transdermal patch, eye drops, gels, ointments, orally, intraocular injection, subconjuctival injection, peri-/retrobulbar injection, transdermally, or topically to the ocular region by an eye drop dispenser, or the like, including topical intranasal administration or administration by inhalant, and the like, spray, emulsion, suspension, via any drug carriers as sponges, contact lenses, polymers, microspheres, and implants. The topical administration can be ophthalmically or intranasally.

Topical ophthalmic products may be packaged in multidose form. Preservatives are thus required to prevent microbial contamination during use. Suitable preservatives include: biguanides, hydrogen peroxide, hydrogen peroxide producers, benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1% (w/w). Unit dose formulations of the present invention will be sterile, but typically unpreserved. Such formulations, therefore, generally will not contain preservatives.

The pharmaceutical composition may further comprise antibiotics. Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, derivatives thereof, and the like and mixtures thereof.

The pharmaceutical composition may further comprise corticosteroids. Examples of corticosteroids include cortisone, prednisolone, triamcinolone, flurometholone, dexamethasone, medrysone, loteprednol, fluazacort, hydrocortisone, prednisone triamcinolone, betamethasone, prednisone, methylprednisolone, triamcinolone acetonide, triamcinolone hexacetonide, paramethasone acetate, diflorasone, fluocinolone and fluocinonide, derivatives thereof, and mixtures thereof.

The pharmaceutical composition may further comprise immunosuppressive agents. Examples of immunosuppresive agents include cyclosporine, azathioprine, tacrolimus, TNFα-inhibitors, infliximab, (Remicade), adalimumab (Humira), certolizumab pegol (Cimzia), and golimumab (Simponi), and etanercept (Enbrel) and derivatives thereof.

The pharmaceutical composition may further comprise antiviral agents. Examples of antiviral agents include and are not limited to, interferon gamma, zidovudine, amantadine hydrochloride, ribavirin, acyclovir, valciclovir, dideoxycytidine, and derivatives thereof.

The pharmaceutical composition may further comprise antihistamines. Examples of antihistamines include, and are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

Treatment Methods

The invention provides a method of treating a disease characterized by ocular inflammation in a subject characterized by increased levels of activated WBCs, by administering to the subject a pharmaceutical composition comprising LtxA and a pharmaceutically acceptable carrier in an amount effective to reduce ocular inflammation characterizing the disease. In another embodiment, the invention provides a method of reducing ocular inflammation in a subject characterized by increased levels of activated WBCs, by administering to the subject a pharmaceutical composition comprising leukotoxin and a pharmaceutically acceptable carrier in an amount effective to reduce ocular inflammation.

Ocular inflammatory disease is characterized by a number of diseases and conditions in which inflammation affects the eye or surrounding tissues. Examples of ocular inflammatory disease include keratoconjunctivitis sicca, diabetic retinopathy, diabetic macula edema, Sjogren syndrome, dry eye, scleritis, birdshot retinochoriodopathy, ocular cicatricial pemphigoid, keratitis, sympathetic ophthalmia, vogt-koyanagi harada, fuchs' heterochromic iridocyclitis, uveitis, pars planitis, episcleritis, optic neuritis, orbital pseudotumor, retinal vasculitis, ocular allergy, chronic conjunctivitis. Many of the above described diseases and inflammation disorders, cause an increase of WBC's expressing the activated conformation of LFA-1 to migrate and congregate in the ocular region and are suitable for treatment by the methods of the present invention.

There is evidence that indicates 'retinal inflammation' contributes to the pathogenesis of diabetic retinopathy. There are common sets of inflammatory cytokines that are upregulated in both the serum and vitreous and aqueous samples, in subjects with diabetic retinopathy, and these cytokines can have multiple interactions to impact the pathogenesis of the disease. The key inflammatory events involved in the blood retinal barrier (BRB) alteration appear to be: (1) Increased expression of endothelial adhesion molecules such as ICAM1, VCAM1, PECAM-1, and P-selectin, (2) adhesion of leukocytes to the endothelium, (3) release of inflammatory chemokines, cytokines, and vascular permeability factors, (4) alteration of adherens and tight junctional proteins between the endothelial cells, and (5) infiltration of leukocytes into the neuro-retina, resulting in the alteration of the blood retinal barrier (diapedesis).

Sjögren's syndrome is an inflammatory disease that can affect many different parts of the body, but most often affects the tear and saliva glands. Patients with this condition may notice irritation, a gritty feeling, or painful burning in the eyes. Membrane bound ICAM-1 is over expressed in the salivary glands (SG) of Sjögren's syndrome (SS) patients.

Dry eye occurs when the eye does not produce tears properly, or when the tears are not of the correct consistency and evaporate too quickly. Dry eye can be associated with inflammation of the surface of the eye, the lacrimal gland, or the conjunctiva.

Conjunctivitis is an inflammation of the conjunctiva. The conjunctiva is the thin, transparent membrane lining that covers the outer surface of the eye. The conjunctiva is nourished by tiny blood vessels that are nearly invisible to the naked eye. The conjunctiva also secretes mucus that moistens and lubricates the eye. Conjunctivitis that persists for four or more weeks is considered chronic. Conjunctivitis can be caused by an infection or by an allergen.

Another condition, allograft rejection is the main cause of graft failure in human corneal transplantation. LFA-1 in conjunction with ICAM-1 has been shown to be important in animal models of corneal graft rejection, thus allograft rejection is another condition that would be suitable for treatment by the methods of the present invention.

A "subject" refers to human and non-human animals. Examples of non-human animals include all vertebrates, e.g., mammals such as non-human primates (particularly higher primates), dogs, rodents (e.g., mice or rats), guinea pigs, cats and non-mammals, such as birds, amphibians, reptiles, etc. In a preferred embodiment, the subject is a human. In another embodiment, the subject is an experimental animal or animal suitable as a disease model.

A subject to be treated for ocular inflammatory disease can be identified by standard diagnosing techniques. Optionally, the subject can be examined for the level or percentage of WBCs that bind to LtxA in a test sample obtained from the subject by methods described below. If the binding level or percentage is at or above a threshold value (which can be obtained from a normal subject), the subject is a candidate for treatment with an effective amount of LtxA.

"Treating" or "treatment" refers to administration of a compound or pharmaceutical composition to a subject, who has an ocular inflammatory disease, with the purpose to cure, alleviate, relieve, remedy, delay the onset of, or ameliorate the disorder, the symptom of the disorder, the disease state secondary to the disorder, or the predisposition toward the disorder.

A "therapeutically effective amount" refers to the amount of an agent or pharmaceutical composition sufficient to effect beneficial or desired results. A therapeutically effective amount can be administered in one or more administrations, applications or dosages and is not intended to be limited to a particular formulation or administration route.

The LtxA pharmaceutical composition can be administered in vivo or ex vivo, alone or co-administered in conjunction with other drugs or therapy. As used herein, the term "co-administration" or "co-administered" refers to the administration of at least two agent(s) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

The LtxA pharmaceutical composition can be administered locally by topically applying the LtxA pharmaceutical composition to the eye in the form of an ointment, gel or droppable liquids using an ocular delivery system known to the art such as an applicator or eyedropper. Alternatively, the LtxA may be administered intraocularly via a polymer implant that is placed under the under the conjunctiva of the eye or through injection directly into the eye.

In another embodiment, a pharmaceutical composition comprising LtxA can be administered systemically. Generally, LtxA is suspended in a pharmaceutically-acceptable carrier (e.g., physiological saline) and administered orally or by intravenous infusion, or injected subcutaneously, intramuscularly, intrathecally, intraperitoneally, intranasally, intragastrically, intratracheally, or intrapulmonarily.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of compounds available and the different efficiencies of various routes of administration. Variations in these dosage levels can be adjusted using standard empirical routines for optimization as is well understood in the art that may be employed by the ordinarily skilled artisan without undue experimentation. Encapsulation of the compound in a suitable delivery vehicle (e.g., polymeric microparticles or implantable devices) may increase the efficiency of delivery.

Diagnostic and Prognostic Methods

Ocular inflammation can be characterized by an increase in active WBCs expressing a greater level of the activated conformation of LFA-1 compared to WBC's of a healthy subject without ocular inflammation. LFA-1, present on WBCs of ocular inflammatory disease patients, can act as a marker to detect and monitor the treatment of these afflictions while providing a therapeutic target for pharmaceutical agents. LtxA specifically targets WBCs that express the activated conformation of LFA-1, and therefore can be used in diagnosing diseases meditated by such WBCs.

In another embodiment, the present invention provides a method to diagnose ocular inflammation characterized by the increase of activated LFA-1 WBCs in the ocular region. WBCs expressing the activated conformation of LFA-1 can be detected in a subject based on the presence of the binding of LtxA in a test sample from the subject. In other words, the binding of LtxA can be used as markers to indicate the presence or absence of WBCs involved in ocular inflammatory disease. Diagnostic and prognostic assays of the invention include methods for assessing the binding level of LtxA with WBCs in the eye and the surrounding tissue.

The binding level in a test sample can be evaluated by obtaining a test sample from a test subject and contacting the test sample with LtxA. The "test sample" includes tissues, cells and biological fluids isolated from a subject, as well as tissues, cells and fluids present within a subject, and from the ocular region. The level of binding of LtxA to WBCs can be measured in a number of ways, including that described in the examples below. In a preferred embodiment, LtxA or its fragments that mediate binding between LtxA and LFA-1 (i.e., probes) are labeled with a detectable agent. The term "labeled" is intended to encompass direct labeling of the probe by physically linking a detectable substance to the probe, as well as indirect labeling of the probe by reactivity with a detectable substance. For example, LtxA (or its fragment) can be indirectly labeled using a second antibody directed against LtxA, wherein the second antibody is coupled to a detectable substance. Examples of detectable substances or labels include radio isotopes (e.g., 125I, 131I, 35S, 3H, or 32P), enzymes (e.g., alkaline phosphatase, horseradish peroxidase, luciferase, or β-glactosidase), fluorescent moieties or proteins (e.g., fluorescein isothiocyanate, rhodamine, phycoerythrin, GFP, or BFP), or luminescent moieties (e.g., Qdot™ nanoparticles by the Quantum Dot Corporation, Palo Alto, Calif.).

LtxA not only binds to, but also kills, WBCs. In the diagnostic or prognostic method, to minimize any potential errors caused by cell death, the binding of LtxA and WBCs can be conducted at low temperatures (e.g., 0-4° C.) and for a short period of time such as 5 to 20 or 30 minutes.

The prognostic assays described herein can be used to determine whether a subject is suitable to be administered with an agent (e.g., a drug) to treat an ocular inflammatory disease. For example, such assays can be used to determine whether a subject can be administered with a cytotoxic drug or immune-suppressants to treat ocular inflammatory disease.

In another embodiment, a biological sample from a subject can also be screened for the increased expression of certain cytokines (biomarkers) to determine whether the subject is in need of a treatment for ocular inflammation. These cytokines/biomarkers include IL-4, IL-5, IL-9, IL-17F and IL-23α. Standard assays are known in the art to detect cytokines in biological samples, including without limitation biological samples isolated from the ocular region.

Thus, also featured in this invention is a method of monitoring a treatment for ocular inflammatory disease in a subject. For this purpose, the binding level between LtxA and WBCs can be determined for test samples from a subject before, during, or after undergoing a treatment. A decrease in the binding level after the treatment indicates that the subject can be further treated by the same treatment. For example, a patient who has received a cornea transplant often faces the problem of tissue rejection. That is, the body has an immune response to a cornea transplant. To address this problem, cornea transplant is often accompanied by nonspecific immune suppression therapy to prevent T cell-mediated rejection. To that end, LtxA's binding level can serve as a marker for a proper level or degree of immune suppression, and/or biomarker expression level be determined compared to the normal cytokine level of a subject without ocular inflammation. A person skilled in the art can adjust the amount of LtxA administered and length of treatment based on the level of the binding during the course of the treatment.

Information obtained from the practice of the above assays is useful in prognostication, identifying progression of, and clinical management of diseases and other deleterious conditions affecting an individual's health status. The information more specifically assists the clinician in designing therapy or other treatment regimens for ocular inflammatory disease.

Kits

In another aspect, the invention provides kits. In one embodiment, a kit containing a pharmaceutically acceptable dose unit of a pharmaceutically effective amount of leukotoxin, and a set of instructions containing methods of treating an ocular inflammatory disorder as described. The kit may further contain an applicator to administer the pharmaceutically acceptable dose unit of a pharmaceutically effective amount of leukotoxin to the ocular region. Ocular applicators are known in the art.

EXAMPLE

Figure 1:
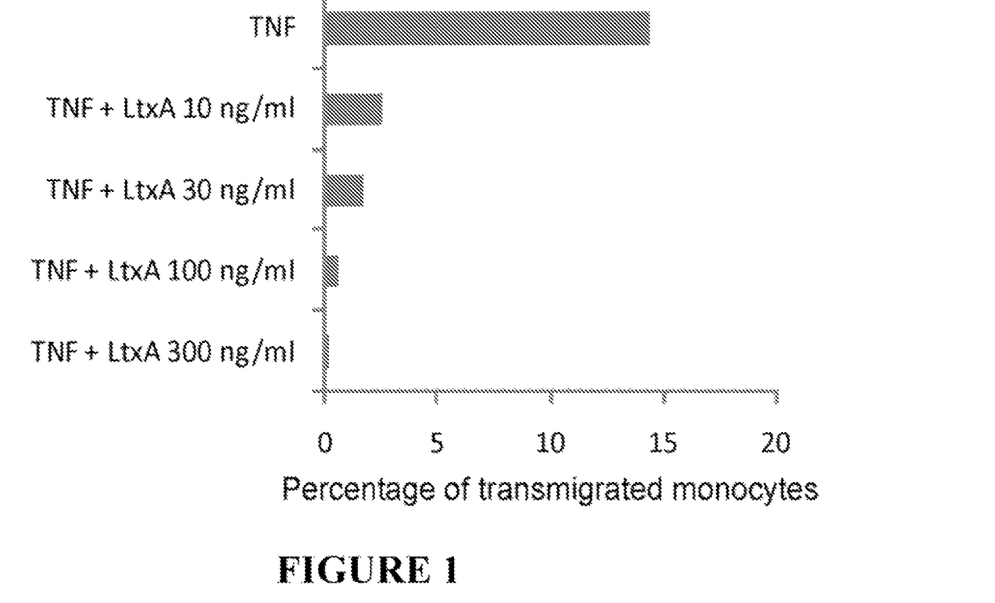
FIG. 1 is a diagram showing migration of white blood cells (WBCs) across an endothelial barrier.

Leukotoxin (LtxA) kills WBCs and prevents migration of WBCs across an endothelial barrier even at doses that do not kill cells (FIG. 1).

Testing to determine if LtxA could block binding of activated PBMCs to human brain endothelial cells (HBECs) to model the initial steps leading to inflammation were carried out. The initial steps leading to inflammation include the binding of activated PBMCs to endothelial cells and migration across the endothelial barrier. Strategies to treat inflammatory response include depletion of those WBCs that are involved in pathogenesis and interruption of their binding and migration into the affected tissue. (Weksler, B. B., E. A. Subileau, N. Perriere, P. Charneau, K. Holloway, M. Leveque, H. Tricoire-Leignel, A. Nicotra, S. Bourdoulous, P. Turowski, D. K. Male, F. Roux, J. Greenwood, I. A. Romero, and P. O. Couraud. 2005. Blood-brain barrier-specific properties of a human adult brain endothelial cell line. Faseb J 19:1872-4.) or (Wassmer, S. C., V. Combes, F. J. Candal, I. Juhan-Vague, and G. E. Grau. 2006. Platelets potentiate brain endothelial alterations induced by *Plasmodium falciparum*. Infect Immun 74:645-53.)

HBECs were grown to monolayer on collagen or gelatin and then stimulated with TNF. Calcein-labeled PBMCs activated with PMA were then added to the monolayer and incubated for 2 hours. Unbound cells were washed and the percent PBMC binding was calculated by measuring fluorescence. LtxA was able to prevent binding of activated PBMCs to the endothelial cells in a dose-dependent manner. Greater than 50% blocking was observed at higher doses of LtxA. Because these PBMCs were from a healthy individual, complete blocking was not observed since most of the cells were normal and not affected by LtxA. Cytotoxicity assays showed that only approximately 10-20% of the cells stained with propidium iodide after two hours thereby indicating that many of the cells that were blocked by LtxA were not killed. LtxA can block the migration of monocytes across a human brain endothelial cell layer (HBECs). LtxA has the ability to selectively deplete and block activated PBMCs from binding to and crossing endothelial cells.

Figure 2:
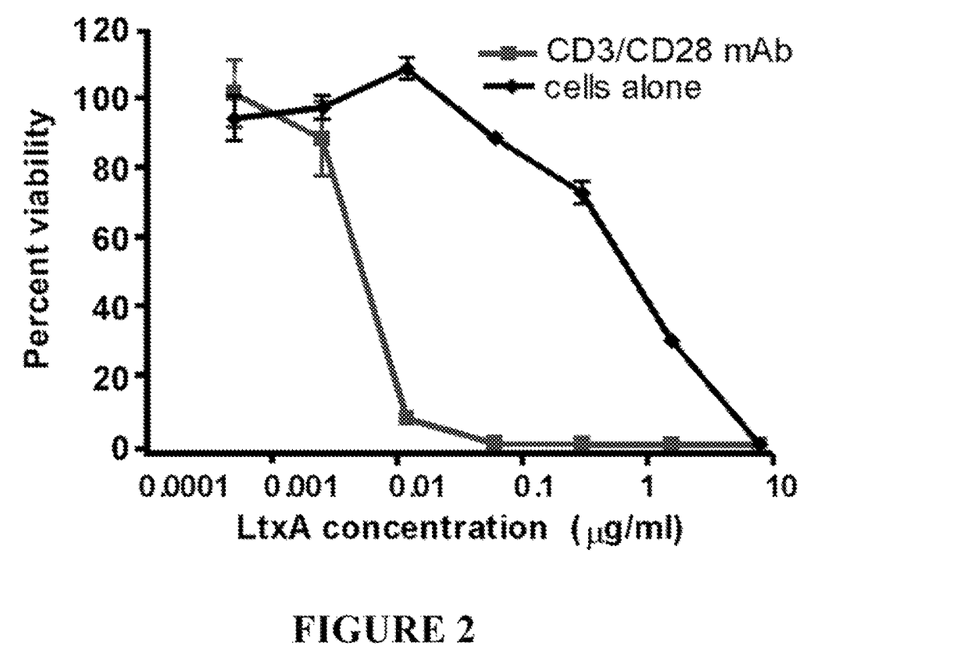
FIG. 2 is a diagram showing sensitivity of activated T-cells.
Figure 3A:
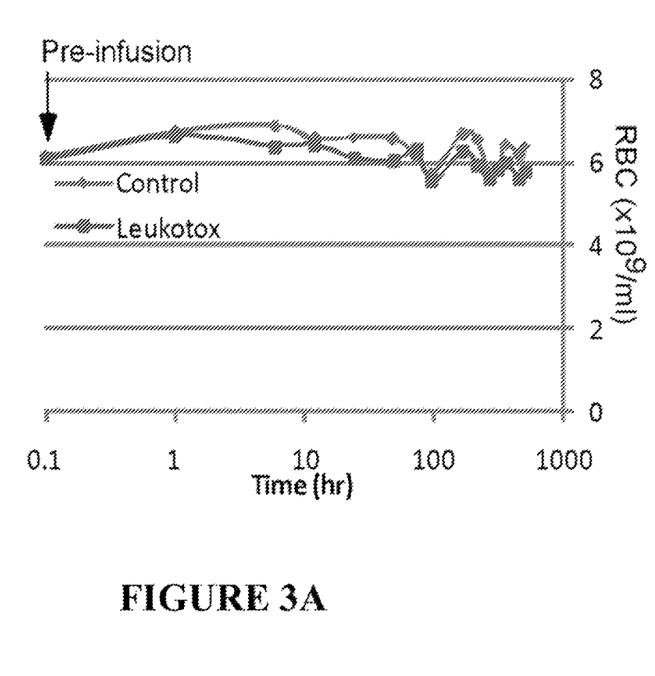
FIGS. 3A, 3B, 3C, 3D, 3E, and 3F are a set of diagrams showing the activity of LtxA under physiologic conditions.
Figure 3B:
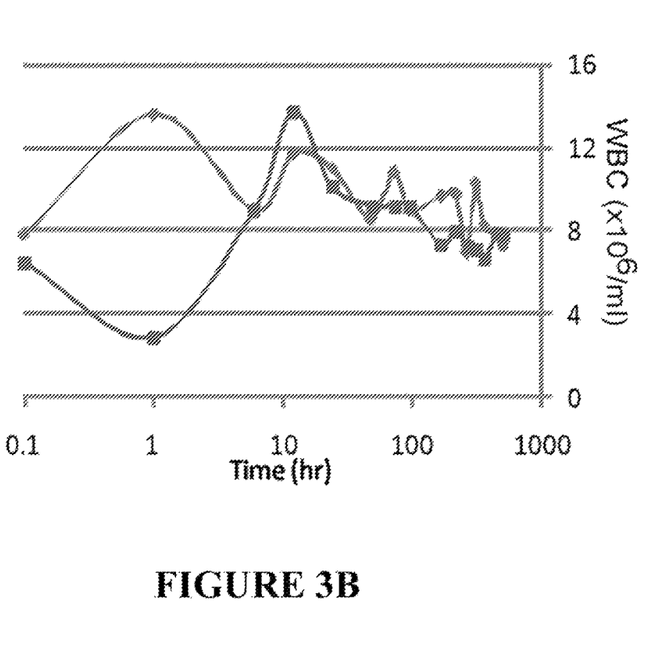
Figure 3C:
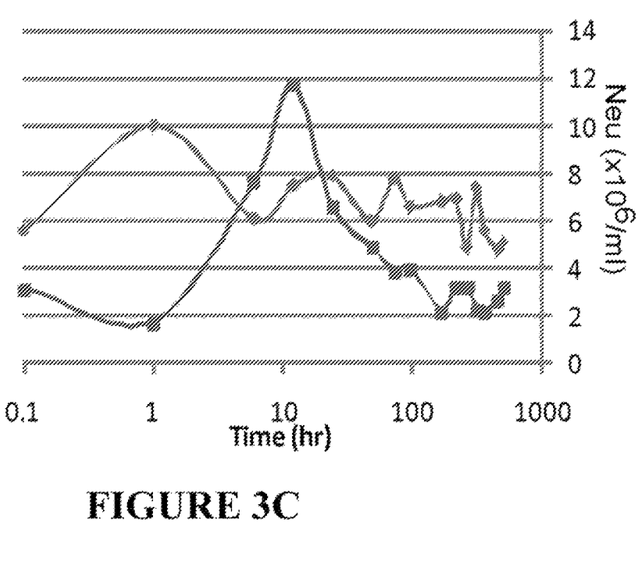
Figure 3D:
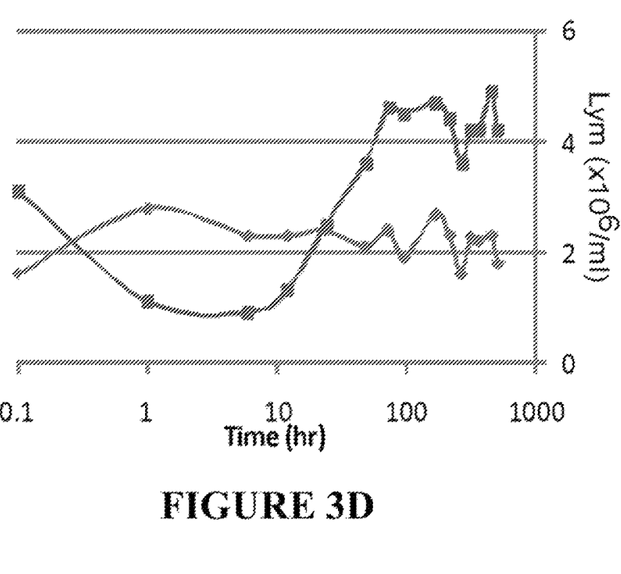
Figure 3E:
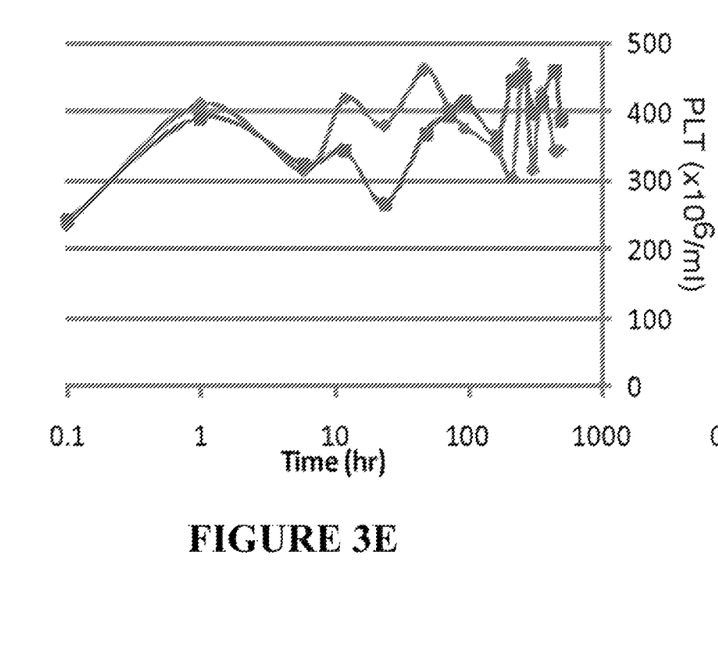
Figure 3F:
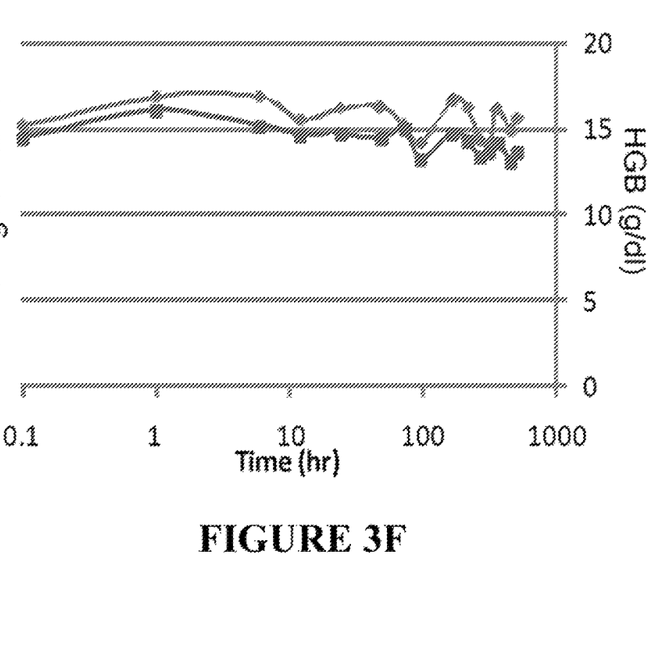
Figure 4:
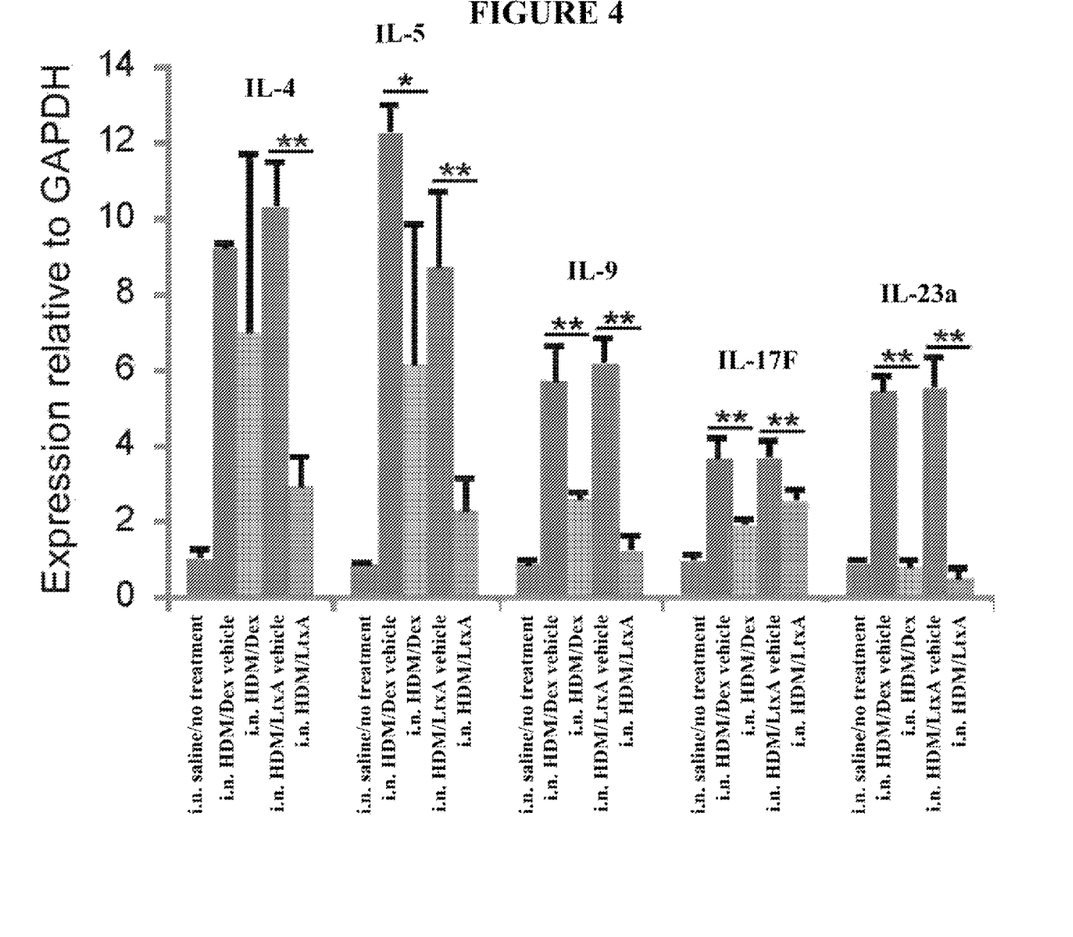
FIG. 4 is a diagram showing the examination of cytokines in lung tissue following treatment of house dust mite (HDM) exposed mice with either a vehicle (saline, HDM/Dex vehicle; or HDM/LtxA vehicle); dexamethasone (HDM/Dex); or leukotoxin (HDM/LtxA).

Next, the specificity of LtxA by examining the effects of LtxA on activated versus non-activated (resting) WBCs was demonstrated. Primary CD4 T-cells were stimulated by cross-linking their T-cell receptor with anti-CD3/CD28 mAb, which is known to cause physiological activation. We then tested the effects of LtxA on activated CD4 T-cells. The activated CD4 T-cells were more than 100-times more sensitive to LtxA than resting T-cells (FIG. 2). Healthy PBMCs were minimally affected by LtxA while the same PBMCs activated ex vivo with 12-O-tetradecanoylphorbol-13-acetate (TPA) were highly sensitive to LtxA-mediated killing. Analysis of LFA-1 on activated cells revealed that LtxA preferentially depletes cells with the highest level of LFA-1 activation as revealed by binding to mAb24, which binds specifically to LFA-1 in the activated state, but not in the resting state.

LtxA was next tested in the rhesus macaque (*Macaca mulatta*) under physiological conditions (FIG. 3A-F). One monkey received a single intravenous infusion of 300 µg LtxA (22 µg/kg) while the second animal served as a control. Throughout the 3-week study, red blood cell (RBC), platelet (PLT), and hemoglobin (HGB) values remained unchanged in the LtxA-treated monkey and were similar to the vehicle-treated control animal. In contrast, the total white blood cell (WBC), Lymphocyte (LYM) and Neutrophil (NEU) count in the treated animal dropped markedly during the first several hours post-infusion and then increased. By 24 hours, counts recovered and long-term myelosuppression was not observed.

Blood chemistry values for the LtxA-treated monkey revealed no change in markers for either liver toxicity (AST, bilirubin, alkaline phosphatase) or kidney function (BUN, creatinine) during the course of the experiment, and animals appeared in good health as evaluated twice daily by the veterinary staff (data not shown). Taken together, these results indicate that LtxA is active and specific in a non-human primate at a non-toxic dose. Primate experiments were carried out at the University of Wisconsin National Primate Research Center (WNPRC) and approved by the University of Wisconsin-Madison Animal Care and Use Committee.

LtxA in solution is highly stable. Soluble LtxA was incubated at room temperature for several days and then tested for bioactivity against a sensitive leukemia cell line (THP-1). LtxA retains full activity even after seven days at room temperature in solution. Similar results were obtained for numerous different preparations of LtxA. We also tested the stability of LtxA at different temperatures. LtxA was incubated for ten minutes at 40, 50, 60, 70, 80, and 90° C. and then tested against THP-1 cells. LtxA was stable up to 60° C. and then began to lose activity. We tested the stability of LtxA at 40° C. and 50° C. over time and found that LtxA retains full activity even after a 4-hour incubation at 40° C. or 50° C. LtxA is also fully stable after ten freeze-thaw cycles.

Immunophenotypic Analysis of WBCs was performed in rhesus monkeys. LtxA (22 μg/kg) was infused i.v. into two monkeys over a twenty-minute period and then blood was drawn from animals at different time points. WBCs were analyzed by flow cytometry. T-cells (CD3+), B-cells (CD20+), and natural killer (NK) cells were depleted by LtxA. NK cells, which have been shown to have an important role in the pathogenesis of inflammatory eye diseases, demonstrated the greatest sensitivity to LtxA. Only the cells with highest levels of LFA-1 were targeted by LtxA. Effector memory T-cells were highly susceptible to LtxA while central memory T-cells were minimally affected and naïve T-cells were not affected. Inflammatory eye diseases, such as dry eye, the effector T-cells exert damaging effects through their functions of inducing overt inflammatory responses even in the absence of antigen in tissues. Regulatory T-cells (Tregs) were not depleted by LtxA. Tregs are an important component of the immune system that prevents excessive immune reactions and can help abrogate autoimmune disease. Thus, LtxA acts on relevant cell types in a highly specific manner, sparing healthy and immunosuppressive cells that are not involved in disease.

Evaluation of LtxA in a Lung Inflammation Mouse Model

Materials and Methods

LtxA Purification: LtxA was purified from culture supernatants of *A. actinomycetemcomitans* strain 4500 (Diaz et al., (2006) Microb Pathog 40, 48-55.)

Animal study. Female BALB/c mice (6-8 weeks, 15-20 g, Jackson Laboratories, Bar Harbor, Me.) were housed under specific pathogen-free conditions and a 12-hour light/dark cycle with access to food and water. Under isoflurane anesthesia, mice were exposed to HDM extract (*D. pteronyssinus*; Greer Laboratories, Lenoir, N.C.) intranasally (25 μg in 10 μl of saline per nostril). Control (non-asthmatic) animals were administered an equal volume of saline alone (saline/no treatment, FIG. 4). The frequency of exposure for HDM/saline was 5 days/week, for a total of 5 weeks. Power calculations from pilot studies indicated that four animals per group were sufficient to detect a significant difference between control and experimental groups.

After two weeks, HDM-exposed mice were divided into 4 groups of 4 mice/group and treated with (1) dexamethasone vehicle, saline (HDM/Dex vehicle, FIG. 4A-B) subcutaneously (s.c.) once daily, five days per week, (2) dexamethasone, Sigma; 1.25 mg/kg (HDM/Dex, FIG. 4) s.c. once daily, five days per week, (3) LtxA vehicle, buffer (HDM/LtxA vehicle, FIG. 4) intraperitoneally (i.p.), three days per week, and (4) LtxA, 0.5 mg/kg (HDM/LtxA, FIG. 4) i.p., three days per week. HDM exposure was continued throughout the 3-week treatment period.

BAL fluid from each mouse was subjected to RBC lysis for 10 minutes at room temperature, followed by washing twice at 400×g for 5 minutes and resuspending the cell pellet in PBS. Total BAL fluid cell number was counted using a hemocytometer. Immunophenotypic analysis of BAL fluid cells was performed by antibody staining and flow cytometry. For each antibody stain, 106 cells were first blocked with Fc blocker (rat anti-mouse CD16/CD32, BD Biosciences, San Jose, Calif.) for 10 minutes at room temperature, followed by incubation with monoclonal antibodies at 4° C. for 30 minutes and analysis on an LSR II flow cytometer (BD Biosciences). Antibodies (BD Biosciences) to the following markers were used to identify the various cellular subtypes: CD3e (T-cells), CD45R/B220 (B-cells), Ly6G, CCR3 (neutrophils), CCR3, Ly6G (eosinophils), MHC II (macrophages). Relevant isotype controls were included with each experiment.

Blood from the mice was collected by ileac vein puncture immediately following the BAL fluid isolation. Blood was collected in anticoagulant tubes and centrifuged at 400×g for 10 minutes.

Lung tissue histology: After collecting BAL fluid and blood, lungs were removed through dissection and stored in 10% neutral buffered formalin at room temperature until microscopic analysis. Sections of paraffin embedded fixed lung tissues were stained with H&E to analyze total lung inflammation. Sections were also stained with periodic acid Schiff reagent to identify mucous and goblet cell hyperplasia and Sirius red for eosinophils. The tissue preparation and examination was carried out at the New Jersey Medical School Histology Core Facility. Samples were examined by a board certified pathologist.

Cytokine Analysis: Quantitative RT-PCR was used to determine the expression levels of proinflammatory cytokines (IL-4, IL-5, IL-9, IL-17F and IL-23α) in the lungs of mice. Total RNA from the lung tissue was extracted with Trizol reagent (Life Technologies, Grand Island, N.Y.). Relative mRNA levels were determined by qRT-PCR. One microgram of total RNA was reverse transcribed using High Capacity cDNA Reverse Transcription Kit (Life Technologies, Grand Island, N.Y.). Amplification was carried out using TaqMan Fast Universal PCR Master Mix (Life Technologies, Grand Island, N.Y.). The data was normalized to GAPDH. Gene expression was calculated using the AACT method relative to naïve sample.

Evaluation of LtxA in a mouse model for allergic asthma. Given the potential role that LFA-1 plays in the pathogenesis of allergic asthma and the ability for LtxA to target specifically the LFA-1hi WBCs ex vivo that are unique to allergic asthma patients, an initial proof-of-principle evaluation of LtxA in a mouse model for allergic asthma was performed. Mice were administered house dust mite (HDM) extract or saline intranasally (i.n.) five days per week for five weeks. After two weeks of administration, HDM-exposed mice were subdivided into four groups of four mice per group and received the following treatments for an additional three weeks: dexamethasone vehicle, subcutaneous (s.c.) 5 days/week; dexamethasone (1.25 mg/kg), s.c. 5 days/week; LtxA vehicle, intraperitoneal (i.p.) 3 days/week; LtxA (0.5 mg/kg), i.p. 3 days/week.

At the end of the study, bronchoalveolar lavage (BAL) fluid, lung tissue, and blood were collected from all mice for further evaluation. Examination of WBCs in the BAL fluid revealed that HDM-exposed mice treated with the dexamethasone vehicle or LtxA vehicle had significantly higher levels of all WBC subsets than mice that were given only saline. Treatment of HDM-exposed mice with dexamethasone or LtxA caused significant reduction in the numbers of WBCs in the BAL fluid.

To determine if LFA-1 is involved in the migration of WBCs to the lung tissue in this animal model, the levels of LFA-1 on PBMCs and BAL fluid WBCs in two HDM-exposed mice that were treated with LtxA vehicle were examined. The migrated WBCs that were present in the BAL fluid had significantly higher levels of LFA-1 than on the WBCs in the peripheral blood of the same animal.

Lung tissue was sectioned and stained with H&E, PAS, or Sirius Red. H&E staining revealed a large infiltration of WBCs in the lung tissue of HDM-exposed mice treated with dexamethasone vehicle or LtxA vehicle. Infiltration was not evident in saline-exposed mice. The infiltration of WBCs in HDM-exposed mice was most evident surrounding the blood vessels and bronchioles. Significant goblet cell hyperplasia surrounding many of the bronchioles in the vehicle-treated controls, but not in the other samples was observed. Staining of polysaccharides with PAS in the lung tissue from LtxA vehicle-treated mice confirmed the presence of mucin-producing goblet cells and subepithelial accumulation of collagen. Sirius Red staining of sections revealed pink-staining eosinophils in the vehicle-treated mice, but not in the LtxA-treated mice. Mice that were treated with dexamethasone had a reduced number of eosinophils compared to the vehicle control, but still greater than LtxA-treated mice.

Proinflammatory cytokines play a crucial role in the pathogenesis of allergic asthma and other inflammatory conditions. In allergic asthma, IL-4, IL-5, IL-9, IL-17F, and IL-23α are the primary signaling molecules involved in disease. The levels of IL-4, IL-5, IL-9, IL-17F, and IL-23α mRNA in the lung tissue from all mice were evaluated (FIG. 9). The vehicle-treated mice had significantly greater expression of the proinflammatory cytokines compared to saline-exposed mice. In addition, dexamethasone caused reduction of IL-9, IL-17F, and IL-23α while LtxA treatment caused significant reduction of all the cytokines that were examined.

All publications cited in the specification publications, are indicative of the level of skill of those reasonably skilled in the art to which this invention pertains. All these publications are herein fully incorporated by reference to the same extent as if each individual publication were specifically and individually indicated as being incorporated by reference.

What is claimed is:

1. A method of treating a disease characterized by ocular inflammation, the method comprising administering a pharmaceutical composition to a subject in need of such treatment in an amount effective to reduce said inflammation, wherein the pharmaceutical composition comprises a leukotoxin comprising SEQ ID NO: 1 and an ophthalmologically acceptable carrier, and wherein the disease is an ocular inflammatory disease, wherein the pharmaceutical composition is administered topically to the ocular region.

2. A method of reducing ocular inflammation in an ocular region within a subject in need thereof, characterized by increased levels of activated white blood cells in a subject in need thereof, the method comprising administering to the subject an amount of a pharmaceutical composition in amount effective to reduce said ocular inflammation, wherein the pharmaceutical composition comprises a leukotoxin comprising SEQ ID NO: 1 and an ophthalmologically acceptable carrier suitable for ocular administration, wherein the pharmaceutical composition is administered topically to the ocular region.

3. The method of claim 1, wherein the leukotoxin is prepared from *Aggregatibacter actinomycetemcomitans*.

4. The method of claim 1, wherein the ocular inflammatory disease is selected from the group consisting of keratoconjunctivitis sicca, diabetic retinopathy, diabetic macula edema, dry eye, scleritis, birdshot retinochoriodopathy, ocular cicatricial pemphigoidm, keratitis, sympathetic ophthalmia, vogt-koyanagi harada, fuchs' heterochromic iridocyclitis, uveitis, pars planitis, episcleritis, optic neuritis, orbital pseudotumor, retinal vasculitis, ocular allergy, and chronic conjunctivitis.

5. The method of claim 1, wherein the amount administered to said subject is effective to reduce local cytokine levels in the ocular region.

6. The method of claim 1, wherein one or more cytokines are selected from the group consisting of IL-4, IL-5, IL-9, IL17F and IL-23α.

7. The method of claim 1, wherein the pharmaceutical composition is formulated for and administered by using an eye drop dispenser.

8. The method of claim 2, wherein the activated white blood cells express a greater level of LFA-1 compared to white blood cells from a normal healthy subject.

9. The method of claim 2, wherein the inflammation is caused by a disease or condition selected from the group consisting of an infection, autoimmune disease, allergen, ocular trauma, and ocular allograft rejection.

10. The method of claim 9, wherein the infection may be caused by a virus, bacteria, or a fungus.

11. The method of claim 1, wherein the ophthalmologically acceptable carrier is selected from the group consisting of an eye gel, eye cream, suspension-type eye drops, eye wash, ointment, gel, liposomal dispersion, colloidal microparticle suspension, implant and a contact lens.

* * * * *